United States Patent [19]

Carleton

[11] 3,956,011
[45] May 11, 1976

[54] METHOD FOR CLEANING DISPOSABLE SUCTION CATHETERS

[76] Inventor: John S. Carleton, 1015 Ellis Ave., Lufkin, Tex. 75901

[22] Filed: May 2, 1974

[21] Appl. No.: 466,216

Related U.S. Application Data

[63] Continuation-in-part of Ser. No. 460,111, April 11, 1974, abandoned.

[52] U.S. Cl. ................................. 134/21; 128/276; 128/350 R; 134/22 C; 134/34; 206/210
[51] Int. Cl.² ..................... B08B 3/04; B08B 9/00; A61M 25/02
[58] Field of Search ............... 134/21, 22 C, 22 R, 134/34; 21/82 H; 128/349 R, 350 R, 276; 206/210, 364

[56] References Cited
UNITED STATES PATENTS

| | | | |
|---|---|---|---|
| 1,336,061 | 4/1920 | Young | 21/82 H UX |
| 1,538,734 | 5/1925 | Oden | 134/21 UX |
| 1,613,185 | 1/1927 | Mitchell | 134/21 |
| 2,233,852 | 3/1941 | Schmitt | 134/21 UX |
| 2,650,179 | 8/1953 | Anderson | 134/21 X |
| 2,702,767 | 2/1955 | Domingo | 134/22 C |
| 3,146,987 | 9/1964 | Krayl | 128/276 |
| 3,584,623 | 6/1971 | Carlisle | 128/276 |
| 3,794,042 | 2/1974 | De Klotz et al. | 206/210 X |
| 3,881,872 | 5/1975 | Naono | 134/21 |

FOREIGN PATENTS OR APPLICATIONS

| | | | |
|---|---|---|---|
| 91,611 | 10/1896 | Germany | 128/349 R |

*Primary Examiner*—Morris O. Wolk
*Assistant Examiner*—Dale Lovercheck

[57] ABSTRACT

Method for cleaning a suction catheter including providing a sterilized environment for the catheter prior to use and convenient vessel for cleaning the catheter between each use with a single patient. The method further includes the steps of cleaning the catheter before each use by securing the suction catheter depending from a holder into an opening in a vessel, the opening mating with the said holder, after using said catheter in connection with treating a patient; flowing a cleaning solution into said vessel to the level of soil on said catheter suspended therein; and suctioning substantially all of said cleaning solution from said vessel through said catheter prior to disposing of both catheter and cleaning system after their use in connection with a single patient.

2 Claims, 6 Drawing Figures

U.S. Patent May 11, 1976 3,956,011
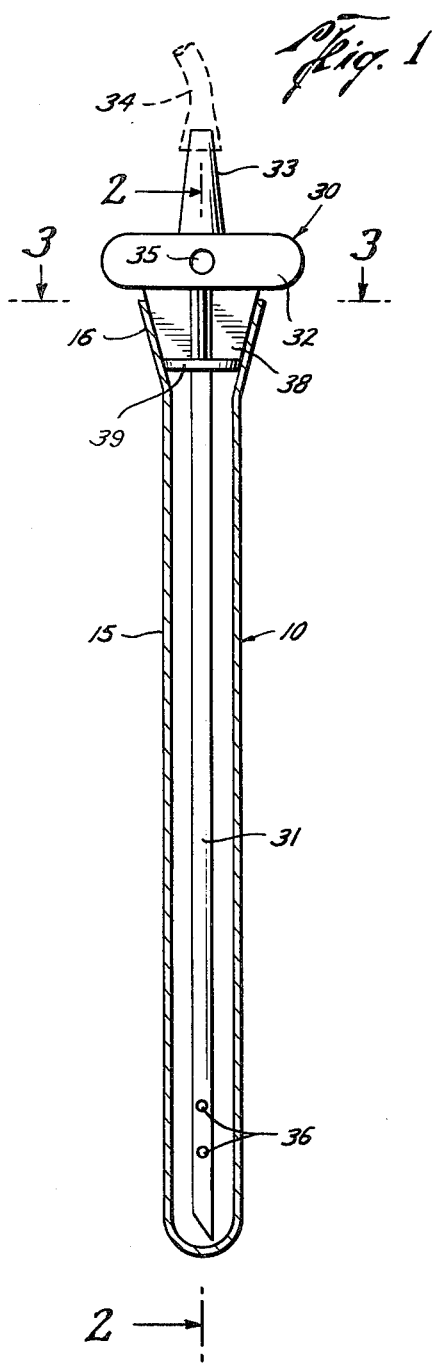
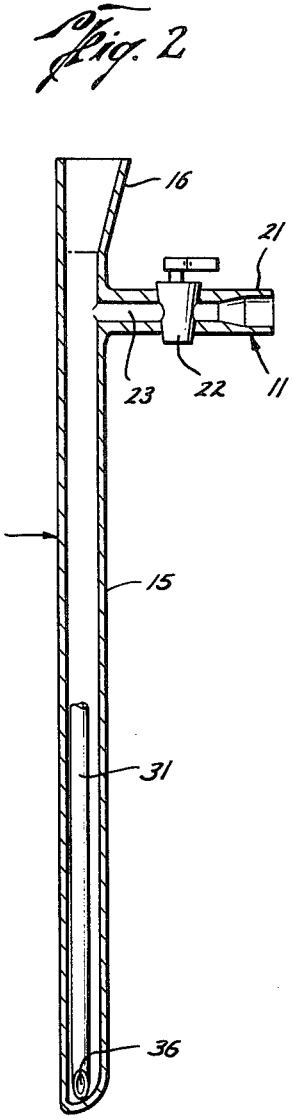
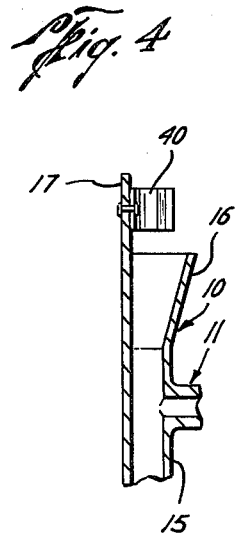
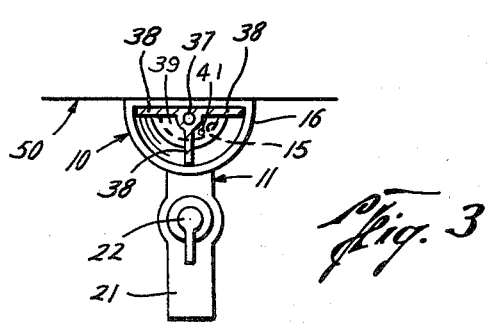
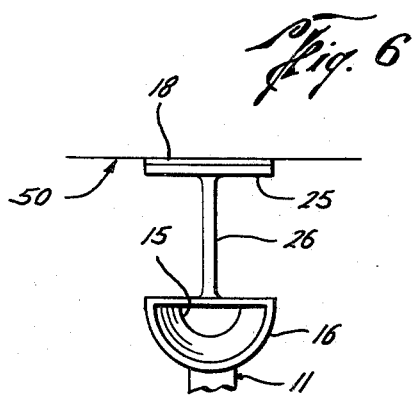

METHOD FOR CLEANING DISPOSABLE SUCTION CATHETERS

CROSS REFERENCES TO RELATED APPLICATIONS

This application is a continuation-in-part of my co-pending application, Ser. No. 460,111, for Disposable Suction Catheter Cleaning System, filed Apr. 11, 1974 and now abandoned.

BACKGROUND OF THE INVENTION

1. Field of the Invention
Suction catheters and catheter cleaning equipment.
2. Description of the Prior Art When utilizing a suction catheter in connection with treating a patient, problems are sometimes encountered in holding the catheter in an appropriate receptacle and in keeping the catheter clean between uses. No satisfactory holder which preserves the cleanliness of the instrument is available at a reasonable cost. Various receptacles have been used for holding the catheters, but they are expensive or are not susceptible of use as a cleaning vessel. Generally exemplary of the state of the art for catheters are U.S. Pat. Nos. 1,161,261; 2,173,527; 2,727,508; and 3,419,009. Generally exemplary of the art of catheter receptacles are U.S. Pat. Nos. 1,120,549 and 3,154,080.

SUMMARY OF THE INVENTION

The apparatus of the invention provides a sterile receptacle for handling the catheter prior to using the catheter, and an inexpensive and conveniently used vessel for cleaning the catheter between uses. The method steps of the invention disclose the use of the apparatus in connection with a disposable catheter for a single patient.

BRIEF DESCRIPTION OF THE DRAWINGS

In the drawings, which illustrate embodiments of the invention presently preferred by the inventor, like numerals and letters refer to like parts, and;

FIG. 1 is a front sectional view of the vessel having a catheter disposed therein.

FIG. 2 is a side elevation sectional view along line 2—2 of the vessel shown in FIG. 1.

FIG. 3 is a plan view, partially in section, taken along line 3—3 of FIG. 1.

FIG. 4 is a partial side elevation view in section of one embodiment of the invention showing alternate means of holding a catheter therein.

FIG. 5 is a top plan view of the embodiment shown in FIG. 4.

FIG. 6 is a top plan view of one embodiment of the invention showing a mounting extension for adhering the vessel to a wall or the like.

DESCRIPTION OF THE PREFERRED EMBODIMENT

The presently preferred embodiment of the apparatus of the invention is shown in FIGS. 1–6 in the drawings. For purposes of illustration, a suctioning catheter 30 is included in FIGS. 1, 2 and 3 to more fully describe the catheter cleaning system disclosed herein. The apparatus of the invention includes a vessel generally designated by the numeral 10, having therein means for transferring a cleaning solution to said vessel. The transferring means conveniently takes the form of a side neck connection generally designated by the numeral 11. Vessel 10 includes a frusto-cylindrical portion 15 and a flared frusto-conical portion 16 therein. Frusto-cylindrical portion 15 is adapted to receive the lower portion 31 of catheter 30 and frusto-conical portion 16 is adapted to receive in mating engagement the wedge portion 38 of catheter 30. A closure 39 is included along a lower portion of wedge portion 38. Closure 39 simply operates as a means of insuring a clean environment for lower portion 31 of catheter 30. Closure 39 may include a small vent 41, or the seal between closure 39 and vessel 10 may be broken when suction is applied or cleaning solution is introduced into vessel 10.

Catheter 30 shown in FIG. 1 is a "whistle-tip" catheter of conventional construction except for wedge shaped portion 38 and closure 39. Catheter 30 is used by connecting connector 33 to a hose 34 fluidly connected with a source of suction. Air is continually sucked through aperture 35 in handle 32 through an axial opening 37 (FIG. 3) in connector 33 and through hose 34 when the catheter is not in use. During cleaning, or when in use in connection with a patient, the physician using the catheter closes aperture 35 with his finger or the like, and suction occurs through holes 36, through the tubular opening axially of lower portion 31 and through axial opening 37 continuing through tip 32 and connector 33 to the source of suction connected to hose 34. It should be noted that the bottom of lower portion 31 of catheter 30 should extend to the lower extermity of vessel 10. In this configuration, essentially all of the washing fluid in vessel 10 will be suctioned from vessel 10 as set forth above. A residue could otherwise build up within vessel 10 which could contribute to unclean conditions in vessel 10.

An alternative form of receiver for a catheter is shown in FIGS. 4 and 5. A clip 40 or the like may be mounted on an upwardly extending portion 17 of frusto-conical portion 16 and used to hold hose 34. Other forms of mating engagement may be used for holding a catheter in vessel 10, and this description of the embodiments disclosed should not be construed to limit coverage of the claims herein. Just as with the embodiments shown in FIGS. 1–3 and 6, the flattened back portion 17 may include an adhesive layer 18 (FIG. 6) applied thereto. Adhesive layer 18 may be any conventional adhesive substance which will secure vessel 10 to a wall 50, bedpost (not shown) or the like.

Means for transferring the cleaning solution from a supply thereof to vessel 10 may take the form (as shown in FIG. 2) of side neck 11. Side neck 11 includes a stem portion 21 and a valve 22 which interrupts fluid connection between the supply and vessel 10 in passage 23. Side neck 11 may be connected to rubber tubing or the like (not shown), and in such event, valve 22 may be replaced by a tubing clamp or other means for interrupting flow in passage 23.

FIG. 6 shows another embodiment of the apparatus of the invention in which an extended mount is interposed between the surface on which the vessel is secured and vessel 10. The mount includes a base 25 and an articulated member 26. This embodiment may be used for holding vessel 10 away from a wall or the like on which vessel 10 is secured.

The presently preferred method of the invention includes the steps of inserting catheter 30 into vessel 10 after its use in connection with a patient, flowing a cleaning solution into vessel 10 to a level sufficient to contact the cleaning solution with the area of catheter 30 which has been soiled by use, covering aperture 35 to create suction through holes 36 and suctioning essentially all of the cleaning solution from vessel 10 through catheter 30. The method may include the additional steps of repeating the flowing and suctioning steps until the catheter has been cleaned. The method may also include the steps of re-using the catheter on a patient and after the final use in connection with a single patient, disposing of the catheter and the vessel.

Vessel 10 may additionally be used in connection with sterile packaging techniques to form a receptacle for catheter 30 in the event that catheter 30 and vessel 10 are to be merchandised as a package unit. It is apparent that with modern injection molding techniques, vessel 10 and catheter 30 may be economically prepared and sold as a disposable package, thereby avoiding the necessity for expensive cleaning and sterilization equipment used for catheters in the prior art.

Thus it can be seen from the above description that an economic and effective catheter cleaning system and method for its use have been shown. The above description is intended to be construed as illustrative only for the purpose of teaching those skilled in the art how to make and use the invention. Substitution of equivalent elements and materials and rearrangement of structural elements and steps may be made without departing from the inventive concept, all as would be apparent to one skilled in the art.

What is claimed is:

1. In a method for cleaning suction catheters, the combination of steps comprising:

securing the suction catheter depending from a holder into an opening in a vessel, the opening mating with the said holder, after using said catheter in connection with treating a patient;

flowing a cleaning solution into said vessel to the level of soil on said catheter suspended therein;

and, suctioning substantially all of said cleaning solution from said vessel through said catheter.

2. The method as claimed in claim 1, including the additional step of:

repeating said flowing and suctioning steps until said catheter has been cleaned.

* * * * *